(12) United States Patent
Ezoe et al.

(10) Patent No.: US 7,563,623 B2
(45) Date of Patent: Jul. 21, 2009

(54) BIOSENSOR

(75) Inventors: Toshihide Ezoe, Kanagawa (JP); Taisei Nishimi, Kanagawa (JP); Yukou Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 18 days.

(21) Appl. No.: 11/708,637

(22) Filed: Feb. 21, 2007

(65) Prior Publication Data

US 2008/0038841 A1 Feb. 14, 2008

(30) Foreign Application Priority Data

Feb. 22, 2006 (JP) ............................ 2006-045615

(51) Int. Cl.
*G01N 33/551* (2006.01)
(52) U.S. Cl. .................. 436/524; 385/12; 385/129; 385/130; 422/57; 422/82.11; 427/2.11; 427/2.13; 427/162; 427/163.2; 427/240; 427/241; 427/421.1; 435/287.2; 435/288.7; 435/808; 436/164; 436/525; 436/805
(58) Field of Classification Search .................. 385/12, 385/129, 130; 422/57, 82.11; 435/287.2, 435/288.7, 808; 436/164, 524, 525, 805; 427/2.11, 2.13, 162, 163.2, 240, 241, 421.1
See application file for complete search history.

(56) References Cited

U.S. PATENT DOCUMENTS 4,874,500 A * 10/1989 Madou et al. ............... 204/412
5,242,828 A * 9/1993 Bergstrom et al. ....... 435/287.1
5,250,613 A * 10/1993 Bergstrom et al. ......... 525/54.1
6,472,224 B1 10/2002 Wischerhoff et al.

FOREIGN PATENT DOCUMENTS

| DE | 198 17 180 A1 | 10/1999 |
|----|---------------|---------|
| JP | 2003-075448 A | 3/2003 |
| JP | 2006-170832 A | 6/2006 |
| WO | 90/05303 A | 5/1990 |
| WO | 2007/043498 A | 4/2007 |

OTHER PUBLICATIONS

Aoki Hiroshi et al., "Ion-channel sensors for electrochemical detection of DNA based on self-assembled PNA monolayers." Nucleic Acids Research Supplement No. 2 P131-132, 2002. XP-002433014.
European Search Report dated Jun. 12, 2007.

* cited by examiner

*Primary Examiner*—Christopher L Chin
(74) *Attorney, Agent, or Firm*—Sughrue Mion, PLLC

(57) ABSTRACT

It is an object of the present invention to provide a biosensor on which a large amount of protein can be immobilized and nonspecific adsorption is less likely to occur with the use of a SAM compound having high water solubility and good performance in terms of supply. The present invention provides a biosensor comprising a substrate on which a hydrophilic polymer having a reactive group capable of binding to a physiologically active substance is immobilized via a compound represented by the following formula (1), said compound at a concentration of 1 mM being dissolved in water at 25° C.:

X-L-Y  (1)

wherein X represents a group capable of binding to metal, L represents a linking group, and Y represents a functional group to which the hydrophilic polymer is bound.

18 Claims, No Drawings

BIOSENSOR

TECHNICAL FIELD

The present invention relates to a biosensor, a method for producing the same, and a method for analyzing interaction between biomolecules with the use of such biosensor. In particular, the present invention relates to a biosensor used as a surface plasmon resonance biosensor, a method for producing the same, and a method for analyzing interaction between biomolecules with the use of such biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

Japanese Patent No. 2815120 discloses a surface to which a hydrogel matrix is bound via a compound forming a self-assembled monolayer (SAM compound), as an example of a detection surface having a functional group capable of immobilizing a physiologically active substance. Specifically, a layer comprising 16-mercaptohexadecanol binds to a gold film, resulting in the formation of a barrier layer. On the gold film, a hydroxyl group of the barrier layer is treated with epichlorohydrin so as to be epoxy-activated. In the subsequent step, dextran is allowed to bind to the barrier layer via an ether bond. Then, bromoacetic acid is allowed to react with a dextran matrix, resulting in introduction of a carboxymethyl group.

However, the mass production of sensors with the use of the SAM compound having a carbon chain with a carbon number of 10 or more described in Japanese Patent No. 2815120 involves the following problems: (1) it is necessary to use a large amount of a solvent for the formation of a film because of the insolubility of SAM compounds, resulting in increased burdens on the global environment, and leading to concerns regarding the health of production workers; (2) the starting materials are not widely distributed, and thus many steps are required for synthesizing such compound, resulting in high costs and difficulties in terms of supply; and (3) denaturation of plastic is likely to be caused when a sensor substrate is made of plastic.

DISCLOSURE OF INVENTION

It is an object of the present invention to solve the aforementioned problems of the prior art. That is, it is an object of the present invention to provide a biosensor on which a large amount of protein can be immobilized and nonspecific adsorption is less likely to occur with the use of a SAM compound having high water solubility and good performance in terms of supply.

As a result of intensive studies to solve the aforementioned problems, the present inventors have found that it is possible to produce a biosensor on which nonspecific adsorption is less likely to occur and a large amount of protein can be immobilized by allowing hydrogel to bind to such biosensor via an SAM compound having high water solubility and good performance in terms of supply. This has led to the completion of the present invention.

Thus, the present invention provides a biosensor comprising a substrate on which a hydrophilic polymer having a reactive group capable of binding to a physiologically active substance is immobilized via a compound represented by the following formula (1), said compound at a concentration of 1 mM being dissolved in water at 25° C.:

X-L-Y (1)

wherein X represents a group capable of binding to metal, L represents a linking group, and Y represents a functional group to which the hydrophilic polymer is bound.

Another aspect of the present invention provides a biosensor comprising a substrate on which a hydrophilic polymer having a reactive group capable of binding to a physiologically active substance is immobilized via a compound represented by the following formula (1):

X-L$^1$-Y (1)

wherein X represents a group capable of binding to metal, L$^1$ represents a C$_2$-C$_{10}$ linear alkylene group optionally interrupted by a hetero atom, and Y represents a functional group to which the hydrophilic polymer is bound.

Preferably, X is an asymmetric or symmetric disulfide group, sulfide group, diselenide group, selenide group, thiol group, nitrile group, isonitrile group, nitro group, selenol group, trivalent phosphorus compound, isothiocyanate group, xanthate group, thiocarbamate group, phosphine group, thioacid group, or dithioacid group.

Preferably, Y is a carboxy group, hydroxyl group, amino group, aldehyde group, hydrazide group, carbonyl group, epoxy group, or vinyl group.

Preferably, X is a thiol group and Y is an amino group.

Preferably, the reactive group capable of binding to a physiologically active substance in the hydrophilic polymer is an activated carboxylic acid ester group.

Preferably, the substrate surface is coated with a mixture of alkanethiol having an amino group and alkanethiol having a hydrophilic group, and the hydrophilic polymer having a reactive group capable of binding to a physiologically active substance is immobilized via alkanethiol having an amino group.

Preferably, the hydrophilic group of alkanethiol having a hydrophilic group is a hydroxyl group or an oligoethylene glycol group.

Preferably, the molar ratio of alkanethiol having an amino group to alkanethiol having a hydrophilic group in a mixture thereof is a molar ratio between 1:1 and 1:1,000,000.

Preferably, the hydrophilic polymer is a polysaccharide.

Preferably, the substrate has a metal surface or is a metal film.

Preferably, the metal is gold, silver, copper, platinum, or aluminium.

Preferably, the substrate is placed on a plastic support.

Preferably, the biosensor of the present invention is used for surface plasmon resonance analysis.

Further another aspect of the present invention provides a method for producing the biosensor according to claim 1, which comprises a step of allowing a hydrophilic polymer having a reactive group capable of binding to a physiologically active substance to come into contact with a substrate coated with a compound represented by the following formula (1), said compound at a concentration of 1 mM being dissolved in water at 25° C., thereby allowing the hydrophilic polymer to bind to the compound represented by the formula (1):

$$X\text{-}L\text{-}Y \qquad (1)$$

wherein X represents a group capable of binding to metal, L represents a linking group, and Y represents a functional group to which the hydrophilic polymer is bound.

Further another aspect of the present invention provides a method for producing the biosensor according to claim 2, which comprises a step of allowing a hydrophilic polymer having a reactive group capable of binding to a physiologically active substance to come into contact with a substrate coated with a compound represented by the following formula (1), thereby allowing the hydrophilic polymer to bind to the compound represented by the formula (1):

$$X\text{-}L^1\text{-}Y \qquad (1)$$

wherein X represents a group capable of binding to metal, $L^1$ represents a $C_2$-$C_{10}$ linear alkylene group optionally interrupted by a hetero atom, and Y represents a functional group to which the hydrophilic polymer is bound.

Preferably, the substrate is coated with a mixture of alkanethiol having an amino group and alkanethiol having a hydrophilic group, and the hydrophilic polymer is allowed to bind to alkanethiol having an amino group.

Preferably, the hydrophilic group of alkanethiol having a hydrophilic group is a hydroxyl group or an oligoethylene glycol group.

Preferably, the molar ratio of alkanethiol having an amino group to alkanethiol having a hydrophilic group in a mixture thereof is a molar ratio between 1:1 and 1:1,000,000.

Preferably, the hydrophilic polymer having a reactive group capable of binding to a physiologically active substance is allowed to react with the compound represented by the formula (1) in such a state that a thin film of said polymer is formed on the substrate.

Preferably, thin film is formed on the substrate by a spin coating method or a spray coating method.

Further another aspect of the present invention provides a biosensor which is produced by the aforementioned method according to the present invention.

Further another aspect of the present invention provides a method for immobilizing a physiologically active substance on a biosensor, which comprises a step of allowing the aforementioned biosensor according to the present invention and the physiologically active substance to come into contact with each other, thereby allowing the physiologically active substance to bind to the biosensor.

Further another aspect of the present invention provides a method for detecting or measuring a substance interacting with a physiologically active substance, which comprises a step of allowing the aforementioned biosensor according to the present invention, the surface of which the physiologically active substance is bound to via a covalent bond, to come into contact with a test substance.

Preferably, the substance interacting with a physiologically active substance is detected or measured by a nonelectrochemical method, and is more preferably detected or measured by surface plasmon resonance analysis.

BEST MODE FOR CARRYING OUT THE INVENTION

The embodiments of the present invention will be described below.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor of the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

In the present invention, a hydrophilic polymer having a reactive group capable of binding to a physiologically active substance is immobilized on a substrate via a compound represented by the following formula (1), said compound at a concentration of 1 mM being dissolved in water at 25° C.:

X-L-Y (1)

wherein X represents a group capable of binding to metal, L represents a linking group, and Y represents a functional group to which the hydrophilic polymer is bound.

Also, in the present invention, a hydrophilic polymer having a reactive group capable of binding to a physiologically active substance may be immobilized on a substrate via a compound represented by the following formula (1):

X-L$^1$-Y (1)

wherein X represents a group capable of binding to metal, L$^1$ represents a $C_2$-$C_{10}$ linear alkylene group optionally interrupted by a hetero atom, and Y represents a functional group to which the hydrophilic polymer is bound.

Preferably, a compound represented by formula (1) has water solubility, resulting in dissolution of such compound (at 0.1 mM and the most preferably at 1.0 mM) at 25° C. In accordance with the present invention, the level of dissolution is defined by a transmission turbidity method. The baseline derived from water in a measurement cell having an optical path length of 10 mm is obtained. Then, the absorbance at 660 nm of a compound solution is measured. When the absorbance (660 nm) of such compound solution is 0.005 or less, the compound is defined as being dissolved.

Preferably, a solvent in which a compound of formula (1) is dissolved is water. However, organic solvents such as ethanol, methanol, and butylalcohol may be mixed with water. The content of such organic solvent in a mixture is preferably 50% or less, more preferably 20% or less, and further preferably 5% or less. In the most preferable case, such compound is dissolved in water alone. Preferably, the organic solvent in a mixture has miscibility with water. Specifically, preferred examples thereof include alcohols. The most preferable example thereof is ethanol.

In the formula (1), X is a group that can bind to a metal. Specific examples thereof that can be preferably used include asymmetric or symmetric disulfide (—SSR'Y", —SSRY), sulfide (—SR'Y", —SRY), diselenide (—SeSeR'Y", —SeSeRY), selenide (SeR'Y", —SeRY), thiol (—SH), nitrile (—CN), isonitrile, nitro (—NO$_2$), selenol (—SeH), trivalent phosphorus compound, isothiocyanate, xanthate, thiocarbamate, phosphine, and thioacid or dithioacid (—COSH, —CSSH).

In formula (1), L, R, and R' are linking groups. Preferably, such a linking group is in the form of a linear chain (having no branches) for tight conformation, that may be interrupted by a hetero atom in some cases. Also, such linking group is in the form of a hydrocarbon chain that may contain double and/or triple bonds in some cases. The chain length is generally 2 carbon atoms or more, preferably 10 carbon atoms or fewer, and further preferably 9 carbon atoms or fewer. The number of carbon atoms contained in a hydrocarbon chain is further preferably 4 to 10 carbon atoms and particularly preferably 4 to 8 carbon atoms. It is possible to excessively fluorinate such carbon chain in some cases.

Y and Y" represent groups used for binding a hydrophilic polymer. Preferably, Y and Y" represent the same group having a property capable of binding to a hydrophilic polymer (e.g., hydrogel) directly or after activation. Specifically, carboxyl, hydroxyl, amino, aldehyde, hydrazide, carbonyl, epoxy, vinyl, and other groups can be used.

A compound represented by X-L-Y in the form of a monolayer having tight conformation can adhere to a metal surface when a group represented by X binds to a metal.

The term "self-assembled monolayer (SAM)" used herein indicates a super-thin film such as a monomolecular film or an LB film. Such super-thin film is formed by a mechanism of a film material so as to have orderly tissue structure without being externally controlled in a precise manner. Such self assembly results in formation of an ordered structure or pattern of a long length in a non-equilibrium state.

For instance, it is possible to form a self-assembled monolayer by using the aforementioned compound represented by formula (1). Formation of a self-assembled monolayer on a gold surface with the use of a sulfur-containing compound is described in, for example, Nuzzo R G et al., (1983), J Am Chem Soc, vol. 105, pp. 4481-4483; Porter M D et al., (1987), J Am Chem Soc, vol. 109, pp. 3559-3568; and Troughton E B et al., (1988), Langmuir, vol. 4, pp. 365-385.

Synthesis of a compound represented by formula (1) can be carried out in accordance with synthesis procedures with the use of a starting material described in, for example, Scheme 1 on p. 10 of Current Organic Chemistry, 2004, 8, 1763-1797, Applications, Properties and Synthesis of ω-Functionalized N-Alkanethiols and Disulfides—the Building Blocks of Self-Assembled Monolayers (written by Dariusz Witt et al.).

In addition, a method for coating a metal film with the use of a self-assembled monolayer (SAM) has been actively developed by Professor Whitesides et al. (Harvard University). Details of the method are reported in, for example, Chemical Review, 105, 1103-1169 (2005). When gold is used as a metal, an orientational self-assembled monomolecular film is formed with the use of an alkanethiol derivative (where n represents an integer from 2 to 10) represented by the following formula 1 based on the van der Waals force between an Au—S bond and an alkyl chain. A self-assembled monolayer is formed by a very simple method, wherein a gold substrate is immersed in a solution of an alkanethiol derivative. A self-assembled monolayer is formed with the use of a compound (represented by the following formula 1 where X is NH$_2$) so that it becomes possible to coat a gold surface with an organic layer comprising an amino group:

HS(CH$_2$)$_n$X  1

It is possible to form a self-assembled monolayer with the use of alkanethiol having an amino group alone. In addition, it is possible to form a self-assembled monolayer by mixing such alkanethiol with other alkanethiols. When alkanethiols are used for a surface of a biosensor, preferred examples of other alkanethiols used are compounds capable of suppressing the nonspecific adsorption of a physiologically active substance. The aforementioned Professor Whitesides has precisely examined a self-assembled monolayer capable of suppressing the nonspecific adsorption of a physiologically active substance. It has been reported that a self-assembled monolayer that has been formed with alkanethiol having a hydrophilic group is useful for suppressing such nonspecific adsorption (Langmuir, 17, 2841-2850, 5605-5620, 6336-6343 (2001)). In the present invention, preferably, it is possible to use the compounds described in the aforementioned papers as alkanethiols that form mixed monomolecular films with alkanethiols having amino groups. It is preferable to use alkanethiol having a hydroxyl group (represented by the following formula 6) or alkanethiol having an ethylene glycol unit (represented by the following formula 7) as alkanethiol that forms a mixed monomolecular film with alkanethiol having an amino group. (In formula 6, n represents an integer from 2 to 10. In formula 7, n represents an integer from 1 to 8 and m represents an integer from 1 to 4; however, the total number of carbons in the molecule is from 2 to 10.) This is because such alkanethiol is excellent in terms of its capacity for suppression of nonspecific adsorption and is readily obtained.

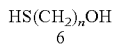     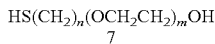

$HS(CH_2)_nOH$         $HS(CH_2)_n(OCH_2CH_2)_mOH$
6                                7

In the present invention, it is possible to mix alkanethiol having an amino group and alkanethiol having a hydrophilic group at an arbitrary ratio. However, when the content of alkanethiol having an amino group is low, the amount of hydrophilic polymer to be bound decreases. When the content of alkanethiol having a hydrophilic group is low, the capacity for suppression of nonspecific adsorption is reduced. Thus, the mixing ratio of alkanethiol having an amino group to alkanethiol having a hydrophilic group is preferably 1:1 to 1:1,000,000, more preferably 1:4 to 1:10,000, and further preferably 1:10 to 1:1,000. In view of reduction of steric hindrance upon a reaction with a hydrophilic polymer, the molecular length of alkanethiol having an amino group is preferably longer than that of alkanethiol having a hydrophilic group.

As alkanethiol used for the present invention, compounds synthesized based on Abstract, Curr. Org. Chem., 8, 1763-1797 (2004) (Professor Grzybowski, Northwestern University) and references cited therein or a commercially available compound may be used. It is possible to purchase such compounds from Dojindo Laboratories, Aldrich, SensoPath Technologies, Frontier Scientific Inc., and the like. In the present invention, disulfide compounds that are oxidation products of alkanethiol can be used in the same manner as alkanethiol.

Next, a hydrophilic polymer having a reactive group capable of binding to a physiologically active substance used in the present invention is described below. As the hydrophilic polymer used in the present invention, a polymeric hardener used for silver halide photography, a hydrophilic polymer having an acetoacetyl group, and a polymer containing an actively esterified carboxyl group can be preferably used. Hereafter, a polymeric hardener used in the present invention, a hydrophilic polymer having an acetoacetyl group, and a polymer containing an actively esterified carboxyl group are described.

A polymeric hardener is a polymer compound that has, within a molecule, a plurality of reactive functional groups that undergo binding reaction with a hydrophilic colloid such as gelatin. Such polymeric hardener is described in the following documents: JP Patent Publication (Kokai) No. 56-66841 A (1981), GB Patent No. 1,322,971, U.S. Pat. No. 3,671,256, JP Patent Publication (Kokai) No. 7-64226 A (1995), JP Patent Publication (Kokai) No. 7-140596 A (1995), J Patent Publication (Kokai) No. 10-111545 A (1998), JP Patent Publication (Kokai) 2000-62629 A, JP Patent Publication (Kokai) No. 2004-20919 A, The Theory of the Photographic Process (written by James, 4$^{th}$ edition, page 84, 1977, Macmillan Publishers Limited), Polymeric Amine and Ammonium Salts (written by Campbelletal et al., pages 321 to 332, 1979, Pergamon Press, Ltd.), and the like.

A polymeric hardener that is used in the present invention is a polymer compound having a reactive functional group capable of binding to a functional group (namely, a group represented by Y in the formula (1)) on the surface of a biosensor. Such polymeric hardener is preferably a polymer compound having a reactive functional group represented by the following formulae (1) to (9).

$—SO_2CH{=}CH_2$                           Formula (1):

$—SO_2CH_2CH_2X$                       Formula (2):

In formula (2), X is a group (e.g., $—Cl$, $—OSO_2CH_3$, $—OSO_2C_6H_4CH_3$, $—OCOCH_3$, $—OSO_3^-$, or pyridinium) that is eliminated by substitution reaction or elimination reaction when the functional group represented by formula (2) reacts with a nucleophilic reagent or a base.

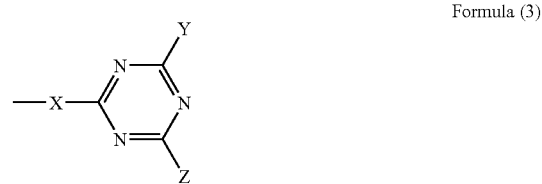

Formula (3)

In formula (3), X represents a single bond, —O—, or —NR— and R represents a hydrogen atom, an alkyl group, or an aralkyl group. Y and Z each represent a halogen atom (e.g., a chlorine atom or a bromine atom), an alkoxy group (e.g., methoxy), a hydroxyl group or a salt thereof, or an amino group that may be substituted. At least one of Y and Z is a halogen atom.

$—CHO$                                        Formula (4):

Formula (5):

Formula (5)

$—NCO$                                        Formula (6):

$—NHCONHCOCH{=}CH_2$               Formula (7):

$—NHCONHCOCH_2CH_2X$              Formula (8):

In the formula, X is as defined in formula (2).

—COX            Formula (9):

In the formula, X is a group (e.g., one of the following groups) that is easily eliminated when the functional group represented by formula (9) reacts with an amino group.

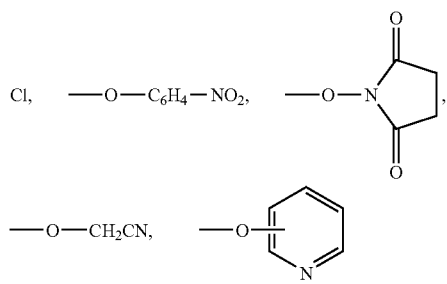

Formula (9) represents a group that is generally known as an active ester group or a mixed anhydride.

A polymerization method used upon production of a polymeric hardener that is used in the present invention is not particularly restricted. For example, such hardener can be produced by a condensation polymerization method. Furthermore, such hardener may also be produced by a method such as radical polymerization or anionic polymerization using compounds having ethylene unsaturated bonds. Furthermore, such hardener may also be produced by introducing the above reactive functional groups into natural polymers (e.g., starch, dextran, and gelatin). A method for introducing a functional group (functional groups represented by the above formulae (1) to (9) and hereinafter referred to as reactive functional groups) that are capable of reacting with a hydrophilic colloid that is used in the present invention is also not particularly restricted. A polymer may also be produced by performing polymerization reaction using monomers having a reactive functional group. Furthermore, a polymer may be previously produced and then the above reactive functional group may also be introduced by so-called polymer reaction. Furthermore, a method that involves performing polymerization reaction using a monomer compound having precursors of a reactive functional group and then generating a reactive functional group by an appropriate method is also effective.

A polymeric hardener that is used in the present invention may also be produced by radically polymerizing monomers having the above reactive functional group (or precursor thereof) and the ethylene unsaturated bond within the same molecule. Typical examples of monomers having a reactive functional group are compounds listed below.

M-1

M-2

M-3
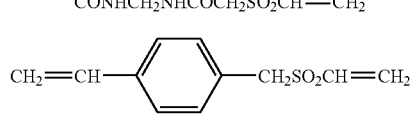

-continued

M-4

M-5

M-6
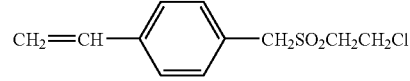

M-7
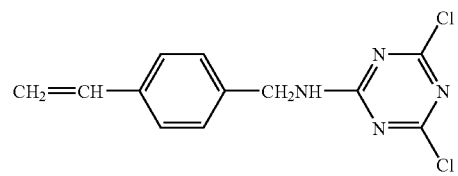

M-8
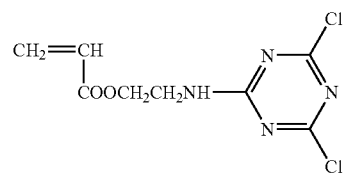

M-9
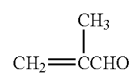

M-10
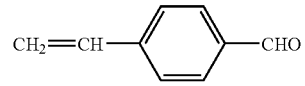

M-11
$CH_3CH=CHCHO$

M-12
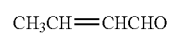

M-13
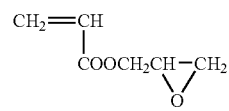

M-14
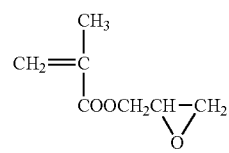

M-15
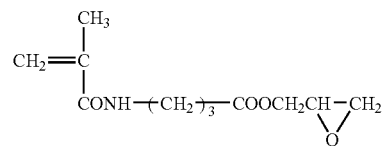

M-16
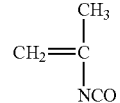

-continued

M-17
$CH_2=CH$
|
$COOCH_2CH_2NCO$

M-18
$CH_3$
|
$CH_2=C$
|
$COOCH_2CH_2NCO$

M-19
$CH_2=CH-\phantom{x}\bigcirc\phantom{x}-CH_2NHCNHCCH=CH_2$
with two C=O groups M-20
$CH_2=CH-\phantom{x}\bigcirc\phantom{x}-CH_2NHCNHCCH_2CH_2Cl$
with two C=O groups M-21
$CH_2=CHCOCl$ M-22
$CH_3$
|
$CH_2=CCOCl$ M-23
$CH_2=CH-\phantom{x}\bigcirc\phantom{x}-COCl$ M-24
$CH_3$
|
$CH_2=C$
|
$COO-\phantom{x}\bigcirc\phantom{x}-NO_2$

M-25
$CH_3$
|
$CH_2=C$
|
$COOCH_2CH_2COSO_2CH_3$
‖
O

M-26
$CH_2=CH$
|
$CONHCH_2CH_2COON$ (succinimide ring)

A polymer that is used in the present invention may be a homopolymer of a monomer having a reactive functional group, or a copolymer of such monomer and another one or two or more different types of monomer. In the case of such copolymer, the proportion of a monomer having a reactive functional group in such copolymer is 1 weight % or more and preferably 5 weight % or more. Radical copolymerization is not particularly limited, as long as the other monomer(s) are radically polymerizable. Specific examples of such monomer include monomers listed below. Furthermore, when the other monomer(s) have a functional group capable of undergoing reaction, it is preferable to select an appropriate combination of monomers within a range such that no reactions are caused to take place upon copolymerization with the functional groups represented by the above formulae (1) to (9).

Such specific examples are: acrylic acid, methacrylic acid, and the esters thereof (e.g., acrylic acid, methylacrylate, butylacrylate, benzylacrylate, hydroxyethylacrylate, $CH_2=CHCOO(CH_2CH_2O)_nR$ (where R is a hydrogen atom or an alkyl group and n is an integer of 1 or greater), methacrylic acid, methyl methacrylate, ethyl methacrylate, benzyl methacrylate, hydroxyethyl methacrylate, 2-ethylhexyl methacrylate, 2-methoxyethyl methacrylate, N,N-dimethylaminoethyl methacrylate, and 2-sulfoethyl methacrylate);

amides of ethylene unsaturated carboxylic acid (e.g., acrylamide, methacrylamide, N-acryloyl morpholine, N,N-dimethylacrylamide, and 2-acrylamide-2-methylpropane sulfonate (or a salt thereof));

aromatic monomers (e.g., styrene, vinyltoluene, p-t-butylstyrene, p-vinylbenzoic acid, and vinylnaphthalene); and other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinylacetoamide, acrylonitrile, and methacrylonitrile).

Specific examples of a polymeric hardener that is used in the present invention will be listed below, but the present invention is not limited by these examples. The copolymerization ratio of each compound represents a weight percentage.

P-1: M-1/2-acrylamide-2-methylpropane sodium sulfonate copolymer (10/90)
P-2: M-1/2-acrylamide-2-methylpropane sodium sulfonate copolymer (30/70)
P-3: M-1/2-acrylamide-2-methylpropane sodium sulfonate copolymer (50/50)
P-4: M-1/methylmethacrylate copolymer (20/80)
P-5: M-2/sodium acrylate copolymer (30/70)
P-6: M-2/2-hydroxyethyl methacrylate copolymer (20/80)
P-7: M-3/butylacrylate copolymer (60/40)
P-8: M-4/2-acrylamide-2-methylpropane sodium sulfonate copolymer (30/70)
P-9: M-6/ethylacrylate copolymer (60/40)
P-10: M-7/N-vinyl pyrrolidone copolymer (20/80)
P-11: M-7/diacetoneacrylamide copolymer (10/90)
P-12: M-10/sodium methacrylate copolymer (15/85)
P-13: M-10/methylacrylate/methylmethacrylate copolymer (20/40/40)
P-14: M-12/ethyl methacrylate copolymer (33/67)
P-15: M-12/2-acrylamide-2-methylpropane sodium sulfonate copolymer (15/85)
P-16: M-13/methyl methacrylate copolymer (33/67)
P-17: M-13/2-acrylamide-2-methylpropane sodium sulfonate copolymer (20/80)
P-18: M-13/N-acryloyl morpholine copolymer (20/80)
P-19: M-13/methoxypolyethylene glycol (23 mer) monomethacrylate copolymer (50/50)
P-20: M-18/N,N-dimethylacrylamide copolymer (5/95)
P-21: M-18/butylmethacrylate copolymer (30/70)
P-22: M-18/styrene/butylacrylate copolymer (20/30/50)
P-23: M-19/2-acrylamide-2-methylpropane sodium sulfonate copolymer (20/80)
P-24: M-23/methylacrylate copolymer (20/80)
P-25: M-24/ethylacrylate/styrene copolymer (20/50/30)
P-26: M-26/acrylamide copolymer (25/75)
P-27: M-26/N,N-dimethylaminoethyl methacrylate copolymer (30/70)

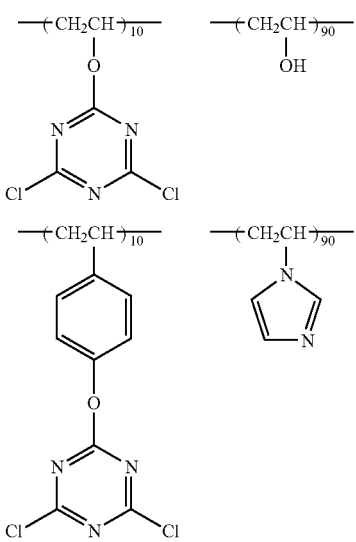

P-28

P-29

As a polymeric hardener having a reactive functional group, which is used in the present invention, preferably, an active olefin type polymeric hardener, an s-triazine type polymeric hardener, an active halogen type polymeric hardener, an aldehyde type polymeric hardener, a glycidyl type polymeric hardener, or the like is used. Further preferably, an active olefin type polymeric hardener or a precursor thereof, an s-triazine type polymeric hardener, or a glycidyl type polymeric hardener is used. A vinylsulfone type polymeric hardener, a precursor thereof, or a dichlorotriazine type polymeric hardener is particularly preferable.

A polymeric hardener in the present invention is immobilized on the surface of a biosensor, in order to form hydrogel. Accordingly, it is desirable that such polymer have hydrophilic groups other than the reactive functional groups. Specific examples of such hydrophilic groups include nonionic groups such as a hydroxyl group and an ethylene glycol group, anionic groups such as a sulfonic acid group, a carboxylic acid group, and a phosphoric acid group, cationic groups such as a quaternary ammonium group and a pyridinium group, and dipolar ionic groups such as a phosphorylcholine group.

Examples of monomer units having a hydrophilic group in the present invention include the following monomers:

monomers having an nonionic group (e.g., 2-hydroxyethylacrylate, 2-hydroxyethyl methacrylate, hydroxypropyl acrylate, hydroxypropylmethacrylate, 2-hydroxy-3-chloropropylacrylate, β-hydroxyethyl β'-acryloyloxyethylphthalate, 1,4-butylene glycol monoacrylate, hydroxystyrene, allylalcohol, methallyl alcohol, isopropenyl alcohol, and 1-butenyl alcohol);

monomers having an anionic group (e.g., vinyl sulfonic acid, methallylsulfonic acid, 2-acrylamide-2-methylpropane sulfonic acid, sulfoethyl methacrylate, styrenesulfonic acid, acrylic acid, methacrylic acid, and 2-(phosphonoethyloxy)ethyl methacrylate); monomers having a cationic group (e.g., [2-(acryloyloxy)ethyl]trimethyl ammonium chloride and [2-(methacryloyloxy)ethyl]trimethyl)ammonium chloride; and monomers having a dipolar ionic group (e.g., [2-(methacryloyloxy)ethyl]dimethyl-(3-sulfopropyl)ammonium hydroxide and [2-(methacryloyloxy)ethyl]phosphorylcholine).

Introduction of cationic group or anionic group into a polymeric hardener enables concentration of a physiologically active substance having opposite charge on a detection surface using electrostatic interaction. For example, in the case of a protein that has been dissolved in a buffer with a pH higher than the isoelectric point, the protein is electrostatically concentrated on the hydrogel surface to which a polymeric hardener having a cationic group has been bound. Thus, it becomes possible to efficiently bind the protein to the reactive functional group. In contrast, in the case of protein that has been dissolved in a buffer with a pH lower than the isoelectric point, the protein is electrostatically concentrated on the hydrogel surface to which a polymeric hardener having an anionic group has been bound. Thus, it also becomes possible to efficiently bind the protein to reactive functional groups. Specific examples of compounds having such a structure may include compounds described below. Moreover, compounds described in JP Patent Publication (Kokai) Nos. 54-65033A (1979), 56-142524A (1981), and 60-61742A (1985) can also be used preferably.

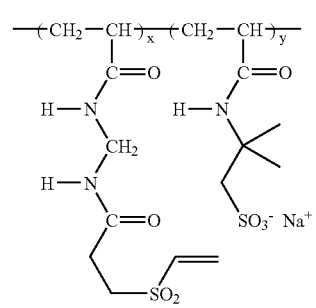

P-30

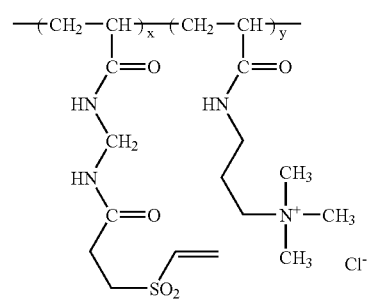

P-31

Hereafter, the hydrophilic polymer having an acetoacetyl group that can be used in the present invention will be explained. An acetoacetyl group-containing water-soluble polymer has the property of reacting with a crosslinking agent having a plurality of aldehyde groups, amino groups, hydrazide groups or the like, at room temperature, so that it becomes hardened. Therefore, it becomes possible to instantly adhere two substrates to each other by applying an acetoacetyl group-containing water-soluble polymer on the surface of one substrate and applying a crosslinking agent on the surface of another substrate, and then by pressing both surfaces. Also, by adding a crosslinking agent to an aqueous solution that contains an acetoacetyl group-containing water-soluble polymer and mixing them, an irrefrangible gel with extremely large water content can be easily obtained at room temperature. JP Patent Publication (Kokai) No. 5-112771 A (1993), JP Patent Publication (Kokai) No. 5-156220 A (1993), JP Patent Publication (Kokai) No. 2002-285117 A, and the like disclose that an acetoacetyl group-containing water-soluble polymer has an excellent property as a water-soluble adhesive.

A method for producing an acetoacetyl group-containing water-soluble polymer will be explained below. Known methods for producing acetoacetylated polyvinyl alcohol, which is a typical compound as an acetoacetyl group-containing water-soluble polymer, include: a method of adding diketene gas to acetic acid in a state where a polyvinyl alcohol resin is dispersed in the acetic acid; a method of adding diketene gas to a solution in which polyvinyl alcohol resin is dissolved in a solvent such as dimethylformamide or dioxane; a method of allowing polyvinyl alcohol powders to directly react with diketene gas; and a method of allowing polyvinyl alcohol to react with an acetoacetic acid ester in a solution for interesterification. The acetoacetylated polyvinyl alcohol used in the present invention can be synthesized by the method described in JP Patent Publication (Kokai) No. 2002-285117 A, for example. Alternatively, commercially available acetoacetylated polyvinyl alcohols such as Gohsefimer Z100, Z200, Z200H, Z210, Z320, or the like, which are made by The Nippon Synthetic Chemical Industry Co., Ltd., can also be used.

Also, an acetoacetyl group-containing water-soluble polymer can be produced via copolymerization of an acetoacetyl group-containing monomer with a water-soluble monomer. Examples of such an acetoacetyl group-containing monomer may include acetoacetoxyethyl acrylate, acetoacetoxyethyl methacrylate, acetoacetoxyethyl crotonate, acetoacetoxypropyl acrylate, acetoacetoxypropyl methacrylate, acetoacetoxypropyl crotonate, 2-cyanoacetoacetoxyethyl methacrylate, N-(2-acetoxyethyl)acrylamide, N-(2-acetoxyaminoethyl) methacrylamide, allyl acetoacetate, and vinyl acetoacetate. These monomers can be produced via a reaction between a functional group-containing ethylene unsaturated monomer and diketene, via a transesterification of the above monomer with an acetoacetoxyalkyl ester, or the like. The acetoacetyl group-containing water-soluble polymer in the invention can be synthesized by the method described in Japanese Patent No. 2777732, for example.

In the present invention, as an acetoacetyl group-containing water-soluble polymer, it is possible to use copolymers with various monomers, other than the aforementioned acetoacetyl group-containing monomer. The monomer unit for such copolymer includes the following monomers:

acrylic acid, methacrylic acid, and their esters: such as acrylic acid, methyl acrylate, butyl acrylate, benzyl acrylate, hydroxyethyl acrylate, $CH_2=CHCOO(CH_2CH_2O)_nR$ (wherein R is a hydrogen atom and an alkyl group, and n is an integer of 1 or greater), methacrylic acid, methyl methacrylate, ethyl methacrylate, benzylmethacrylate, hydroxyethyl methacrylate, 2-ethylhexyl methacrylate, 2-methoxyethyl methacrylate, N,N-dimethylaminoethyl methacrylate, and 2-sulfoethyl methacrylate;

amides of ethylene unsaturated carboxylic acid: such as acrylamide, methacrylamide, N-acryloyl morpholine, N,N-dimethylacryl amide, and 2-acrylamide-2-methylpropane-sulfonic acid (or its salt);

aromatic monomers: such as styrene, vinyl toluene, p-t-butylstyrene, p-vinyl benzoic acid, or vinylnaphthalene; and other vinyl monomers: such as ethylene, propylene, vinyl chloride, vinylidene chloride, trifluoroethylene, trifluorochloroethylene, vinyl acetate, vinyl propionate, vinyl alcohol, N-vinyl pyrrolidone, N-vinylacetamide, acrylonitrile, or methacrylonitrile.

In the invention, an acetoacetyl group-containing hydrophilic polymer is immobilized on the surface of a biosensor, so as to form a hydrogel thereon. Therefore, it is preferable that such an acetoacetyl group-containing hydrophilic polymer have a hydrophilic group as well as a reactive functional group. Specific examples of such a hydrophilic group may include nonionic groups such as a hydroxyl group or an ethylene glycol group, anionic groups such as a sulfonic group, a carboxylic acid, or a phosphate group, cationic groups such as a quaternary ammonium group or a pyridinium group, and zwitterionic groups such as phosphoryl choline group.

In the invention, monomer units having a hydrophilic group include the following monomers:

monomers having a nonionic group: 2-hydroxyethyl acrylate, 2-hydroxyethyl methacrylate, hydroxypropyl acrylate, hydroxypropyl methacrylate, 2-hydroxy-3-chloropropyl acrylate, β-hydroxyethyl-β'-acryloyloxyethyl phthalate, 1,4-butylene glycol monoacrylate, hydroxystyrene, allyl alcohol, methallyl alcohol, isopropenyl alcohol, 1-butenyl alcohol, or the like;

monomers having an anionic group: vinylsulfonic acid, methallylsulfonic acid, 2-acrylamide-2-methylpropane-sulfonic acid, sulfoethyl methacrylate, styrenesulfonic acid, acrylic acid, methacrylic acid, 2-(phosphonoethyloxy)ethyl methacrylate, or the like;

monomers having a cationic group: [2-(acryloyloxy)ethyl] trimethylammonium chloride, [2-(methacryloyloxy)ethyl] trimethylammonium chloride, or the like; and monomers having a zwitterionic group: [2-(methacryloyloxy)ethyl]dimethyl-(3-sulfopropyl)ammonium hydroxide, 2-[(methacryloyloxy)ethyl]phosphorylcholine, or the like.

By introducing a cationic group or an anionic group into an acetoacetyl group-containing water-soluble polymer, a physiologically active substance having opposite charges can be concentrated onto a detection surface via an electrostatic interaction. In the case of a protein dissolved in a buffer solution having a pH that is higher than an isoelectric point, for example, since such a physiologically active substance is electrostatically concentrated onto a hydrogel surface, to which an acetoacetyl group-containing hydrophilic polymer having a cationic group is bound, it can be effectively bonded to a reactive functional group. On the other hand, in the case of a protein dissolved in a buffer solution having a pH that is lower than an isoelectric point, since such a physiologically active substance is electrostatically concentrated onto a hydrogel surface, to which an acetoacetyl group-containing water-soluble polymer having an anionic group is bound, it becomes possible to allow the physiologically active substance to efficiently react with an acetoacetyl group or a carboxylic acid introduced by allowing such an acetoacetyl group to react with amino acid.

Next, the polymer containing an actively esterified carboxyl group that is used in the present invention is described below. The polymer containing an actively esterified carboxyl group used in the present invention can be prepared by allowing the carboxyl group of a polymer containing a carboxyl group to be actively esterified. Examples of a polymer containing a carboxyl group that can be used include a synthetic polymer containing a carboxyl group and polysaccharide containing a carboxyl group. Examples of a synthetic polymer containing a carboxyl group include polyacrylic acid, polymethacrylic acid, and copolymers of such acids, including methacrylic acid copolymer, acrylic acid copolymer, itaconic acid copolymer, crotonic acid copolymer, maleic acid copolymer, partially esterified maleic acid copolymer, and a polymer containing a hydroxyl group to which acid anhydride is added described in JP Patent Publication (Kokai) No. 59-44615 A (1984), JP Patent Publication (Kokoku) No.

54-34327 B (1979), JP Patent Publication (Kokoku) No. 58-12577 B (1983), JP Patent Publication (Kokoku) No. 54-25957 B (1979), JP Patent Publication (Kokai) No. 59-53836 A (1984), and JP Patent Publication (Kokai) No. 59-71048 A (1984). A polysaccharide containing a carboxyl group may be extracts from natural plants, microbial fermentation products, enzymatically synthesized products, or chemically synthesized products. Specific examples thereof include hyaluronic acid, chondroitin sulfate, heparin, dermatan sulfate, carboxymethyl cellulose, carboxyethyl cellulose, cellouronic acid, carboxymethyl chitin, carboxymethyl dextran, and carboxymethyl starch. As such polysaccharide containing a carboxyl group, it is possible to use a commercially available compound. Specific examples thereof include carboxymethyldextrans such as CMD, CMD-L, and CMD-D40 (Meito Sangyo Co., Ltd.), sodium carboxymethyl cellulose (Wako Pure Chemical Industries, Ltd.), and sodium alginate (Wako Pure Chemical Industries, Ltd.).

A polymer containing a carboxyl group is preferably a polysaccharide containing a carboxyl group and more preferably carboxymethyl dextran.

The molecular weight of the polymer containing a carboxyl group used in the present invention is not particularly limited. However, the average molecular weight is preferably 1,000 to 5,000,000, more preferably 10,000 to 2,000,000, and further preferably 100,000 to 1,000,000. When the average molecular weight is below the aforementioned scope, the amount of physiologically active substance immobilized becomes small. When the average molecular weight exceeds the aforementioned scope, it is difficult to handle the polymer due to a high solution viscosity.

A known technique can be preferably used as a method for activating polymers containing carboxyl groups. Examples of such method include: a method that involves activating carboxyl groups using 1-(3-Dimethylaminopropyl)-3 ethylcarbodiimide (EDC) (water-soluble carbodiimide) and N-Hydroxysuccinimide (NHS); a method disclosed in JP Patent Application No. 2004-238396 (JP Patent Publication (Kokai) No. 2006-58071A) (specifically, the method involves activating carboxyl groups using any one of compounds including a uronium salt, a phosphonium salt, and a triazine derivative having a specific structure); and a method disclosed in JP Patent Application No. 2004-275012 (JP Patent Publication (Kokai) No. 2006-90781A) (specifically, the method involves performing activation using a carbodiimide derivative or a salt thereof, followed by activation of carboxyl groups using any one of compounds including a nitrogen-containing heteroaromatic compound having a hydroxyl group, a phenol derivative having an electron-withdrawing group, and an aromatic compound having a thiol group). It becomes possible to produce the biosensor surface of the present invention by causing a polymer containing a carboxyl group that has been activated by these techniques to react with a substrate having an amino group.

The uronium salt, phosphonium salt, and triazine derivative having a particular structure in Japanese Patent Application No. 2004-238396 (JP Patent Publication (Kokai) No. 2006-58071A) refer to a uronium salt represented by the formula 1 below, phosphonium salt represented by the formula 2 below, and triazine derivative represented by the formula 3 below, respectively.

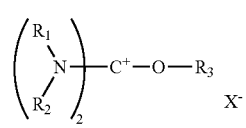

Formula 1

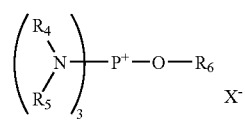

Formula 2

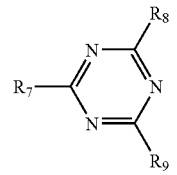

Formula 3

In the formula 1, $R_1$ and $R_2$ each independently represent an alkyl group containing 1 to 6 carbon atoms or together form an alkylene group containing 2 to 6 carbon atoms and form a ring with a N atom, $R_3$ represents an aromatic ring group containing 6 to 20 carbon atoms or a heterocyclic group containing at least one or more heteroatom, and $X^-$ represents an anion. In the formula 2, $R_4$ and $R_5$ each independently represent an alkyl group containing 1 to 6 carbon atoms or together form an alkylene group containing 2 to 6 carbon atoms and form a ring with a N atom, $R_6$ represents an aromatic ring group containing 6 to 20 carbon atoms or a heterocyclic group containing at least one or more heteroatom, and $X^-$ represents an anion. In the formula 3, $R_7$ represents an onium group, and $R_8$ and $R_9$ each independently represent an electron donating group.

In the present invention, a hydrophilic polymer having a reactive group capable of binding to a physiologically active substance may be used in the form of a solution such that such polymer is subjected to a reaction with a substrate. Also, such hydrophilic polymer may be subjected to a reaction after a thin film has been formed on a substrate by a method such as spin coating. It is preferable to carry out such a reaction after formation of a thin film.

As a method for forming a thin film on a substrate, known methods can be used. Specific examples of such methods that can be used include an extrusion coating method, a curtain coating method, a casting method, a screen printing method, a spin coating method, a spray coating method, a slide bead coating method, a slit and spin method, a slit coating method, a dye coating method, a dip coating method, a knife coating method, a blade coating method, a flow coating method, a roll coating method, a wire-bar coating method, and a transfer printing method. These methods for forming a thin film are described in "Progress in Coating Technology (*Coating Gijutsu no Shinpo*)" written by Yuji Harazaki, Sogo Gijutsu Center (1988); "Coating Technology (*Coating Gijutsu*)" Technical Information Institute Co., Ltd. (1999); "Aqueous Coating Technology (*Suisei Coating no Gijutsu*)" CMC (2001); "Evolving Organic Thin Film: Edition for Deposition (*Shinka-suru Organic Thin Film: Seimaku hen*)" Sumibe Techno Research Co., Ltd. (2004); "Polymer Surface Processing Technology (*Polymer Hyomen Kako Gaku*)" written by Akira Iwamori, Gihodo Shuppan Co., Ltd. (2005); and the like. As the method for forming a thin film on a substrate of the present invention, a spray coating method or a spin coating method is preferable. Further, a spin coating method is more preferable. This is because it allows a coating film having a controlled film thickness to be readily produced.

The spray coating method is a method wherein a substrate is moved with an ultra-atomized polymer solution sprayed onto the substrate to thereby uniformly coat the polymer solution onto the substrate. When the trigger of a spray gun is pulled, an air valve and a needle valve are simultaneously opened. The polymer solution is ejected in the form of a fine mist from a nozzle, and this polymer solution in the form of a fine mist is further ultra-atomized by air ejected from an air cap located at the end of the nozzle. A thickness-controlled polymer film is easily produced by forming the coating film of the ultra-atomized polymer solution on the substrate surface, followed by the evaporation of the solvent. The thickness of the polymer thin film can be controlled on the basis of the concentration of the polymer solution, the moving speed of the substrate, and so on.

The spin coating method is a method wherein a polymer solution is added dropwise onto a substrate placed horizontally, which is then spun at a high speed to thereby uniformly coat the polymer solution onto the whole surface of the substrate through a centrifugal force. A thickness-controlled polymer film is easily produced with the scattering of the polymer solution through a centrifugal force and the evaporation of the solvent. The thickness of the polymer thin film can be controlled on the basis of the revolution speed, the concentration of the polymer solution, the vapor pressure of the solvent, and so on. In the present invention, the revolution speed during spin coating is not particularly limited. If the revolution speed is too small, the solution remains on the substrate. If the revolution speed is too large, an available apparatus is restricted. Hence, in the present study, the revolution speed during spin coating is preferably 500 rpm to 10,000 rpm, more preferably 1,000 rpm to 7,000 rpm.

In addition to the aforementioned carboxyl group (or actively esterified carboxyl group), examples of a reactive group capable of binding to a physiologically active substance contained in a hydrophilic polymer that may be used include: an amino group protected by a halogen atom, an amino group, or a protecting group; a carbonyl group having a leaving group; a hydroxyl group; a hydroxyl group protected by a protecting group; an aldehyde group; —NHNH$_2$, —N=C=O; —N=C=S; an epoxy group; and a vinyl group.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies agai◯ 407 antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle (θSP) is measured periodically when a certain period of time has elapsed.

If the test substance contained in the sample solution is bound to the sensing substance, the refractive index of the sensing substance is changed by this binding over time. Accordingly, the above attenuated total reflection angle (θSP) is measured periodically after the elapse of a certain time, and it is determined whether or not a change has occurred in the above attenuated total reflection angle (θSP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

SAM compounds described below were separately mixed with water such that they had the concentrations listed in table 1. The mixtures were allowed to stand at 25° C. for one day, followed by observation. Table 1 shows the results based on visual observation. The symbol "x" indicates a resultant in which precipitation and sedimentation were observed, the symbol "Δ" indicates a resultant in which opacity was observed, and the symbol "○" indicates a resultant having an achromatic and transparent color.

16-Hydroxy-1-hexadecanethiol (Frontier Scientific)
11-Hydroxy-1-undecanethiol (Aldrich)
8-Hydroxy-1-octanethiol (Aldrich)
6-Hydroxy-1-hexanethiol (Aldrich)
11-Amino-1-undecanethiol, hydrochloride (Dojindo Laboratories)
8-Amino-1-octanethiol, hydrochloride (Dojindo Laboratories)
6-Amino-1-hexanethiol, hydrochloride (Dojindo Laboratories)

TABLE 1

| HS-(CH2)n-R | | Solubility (solvent (H$_2$O) allowed to stand at 25° C. for one day) SAM concentration (mM) | | | |
|---|---|---|---|---|---|
| R | n | 0.1 | 1 | 5 | 20 |
| OH | 16 | X | X | X | X |
|  | 11 | X | X | X | X |
|  | 8 | ○ | ○ | Δ | X |
|  | 6 | ○ | ○ | ○ | Δ |
| NH2•HCl | 11 |  | Δ | Δ | Δ |
|  | 8 | ○ | ○ | ○ | ○ |
|  | 6 | ○ | ○ | ○ | ○ |

It is understood that 8-Hydroxy-1-octanethiol, 6-Hydroxy-1-hexanethiol, 8-Amino-1-octanethiol, hydrochloride, and 6-Amino-1-hexanethiol, hydrochloride had good water solubility. Meanwhile, 16-Hydroxy-1-hexadecanethiol, 11-Hydroxy-1-undecanethiol, and 11-Amino-1-undecanethiol, hydrochloride were found to be unable to form a self-assembled monolayer (SAM) in the form of a metal film in an aqueous solution system.

Example 2

With the use of an SAM compound having high water solubility, a hydrogel film capable of immobilizing protein was produced. Then, the amount of protein immobilized and the nonspecific adsorption performance were evaluated.

(1) Production of a Substrate

A mixture aqueous solution containing 6-Hydroxy-1-undecanethiol (Aldrich) and 8-Amino-1-octanethiol, hydrochloride (Dojindo Laboratories) was produced. The obtained solution (containing 4.995 mM 6-Hydroxy-1-undecanethiol and 0.005 mM 8-Amino-1-octanethiol, hydrochloride) is referred to as solution A.

Then, a gold thin film was deposited on the top surface of a plastic prism obtained via injection molding with the use of ZEONEX (Zeon Corporation) in accordance with a method described below. A prism was applied to a substrate holder of a sputtering apparatus. After a step of drawing a vacuum (base pressure: $1 \times 10^{-3}$ Pa or less), Ar gas (1 Pa) was introduced into the apparatus. While the substrate holder was allowed to rotate (20 rpm), RF power (0.5 kW) was applied to the substrate holder for approximately 9 minutes such that the prism surface was subjected to plasma treatment. Subsequently, introduction of Ar gas was discontinued. After a step of drawing a vacuum, Ar gas (0.5 Pa) was again introduced into the apparatus. While the substrate holder was allowed to rotate (10 to 40 rpm), DC power (0.2 kW) was applied to an 8-inch Cr target for approximately 30 seconds such that a 2-nm Cr thin film was deposited. Then, Ar gas introduction was terminated. After another step of drawing a vacuum, Ar gas (0.5 Pa) was again introduced into the apparatus. While the substrate holder was allowed to rotate (20 rpm), DC power (1 kW) was allowed to apply to an 8-inch Au target for approximately 50 seconds such that an Au thin film (approximately 50 nm) was deposited.

The thus obtained sensor stick on which the Au thin film was deposited, was immersed in solution A at 40° C. for 1 hour, followed by washing 10 times with ultrapure water.

(2) Active Esterification of CMD (Carboxymethyldextran)

A mixture solution (50 μl) (containing 0.4 M EDC (1-Ethyl-3-[3-Dimethylaminopropyl]carbodiimide Hydrochloride) and 0.1 M NHS (N-hydroxysulfosuccinimide)) was added to 4.95 ml of a solution in which CMD (molecular weight: 1,000,000, Meito Sangyo Co., Ltd.) had been dissolved to become 0.1% by weight, followed by agitation at room temperature. The amount of the mixture solution was calculated in a manner such that all the reactants were subjected to a reaction, resulting in activation of 2% of carboxyl groups.

(3) Binding Reaction of CMD to a Substrate

The actively esterified CMD solution (500 μl) that had been produced in (2) above was added dropwise onto the substrate that had been produced in (1) above, followed by spin coating at 1000 rpm for 45 seconds. Thus, an actively esterified carboxymethyldextran thin film was formed on a substrate having an amino group. The thin film was subjected to a reaction at room temperature for 1 hour, followed by washing 5 times with 0.1 N NaOH and 5 times with ultrapure water. Thus, sample 1 was obtained.

Comparative Example 1

(i) Production of Substrate Having an OH Group

A solution of 5 mM 16-Hydroxy-1-hexadecanethiol (Frontier Scientific) (ethanol:water=8:2) was produced. The obtained solution is referred to as solution B. Then, as with the case of Example 2, a 50-nm gold film was formed on a sensor stick. The sensor stick was immersed in solution B at 40° C. for 60 minutes, followed by washing 5 times with ethanol, 1 time with 50 ml of a mixture (ethanol:water (80:20)), and 5 times with 50 ml of ultrapure water.

(ii) Epichlorohydrin Treatment

The aforementioned substrate was immersed in a mixture solution containing 20 ml of 0.4 M sodium hydroxide, 20 ml of diethylene glycoldimethyl ether, and 2.0 ml of epichlorohydrin, so as to be subjected to a reaction in a shaking incubator at 25° C. for 4 hours. Then, the substrate was washed twice with 50 ml of ethanol and 5 times with 50 ml of water.

(iii) Dextran Treatment

The aforementioned substrate was immersed in a mixture solution of 40.5 ml of water, 13.5 g of dextran (T500, Pharmacia), and 4.5 ml of 1M sodium hydroxide, so as to be subjected to a reaction in a shaking incubator at 25° C. for 20 hours. Then, the substrate was washed 15 times with 50 ml of water at 50° C.

(iv) Treatment with Bromoacetic Acid

The aforementioned substrate was immersed in a mixture solution of 3.5 g of bromoacetic acid and 27 g of a 2 M sodium hydroxide solution so as to be subjected to a reaction in a shaking incubator at 28° C. for 16 hours, followed by washing with water. The substrate was again subjected to a reaction with bromoacetic acid solution for 16 hours, followed by washing with water. Thus, sample 2 was obtained.

Example 3

Example 3 relates to protein immobilization on the sensor samples obtained in Example 2 and Comparative example 1, respectively. The protein used was CA (carbonic anhydrase, SIGMA).

Samples 1 and 2 that had been produced in Example 2 and Comparative example 1, respectively, were introduced into a surface plasmon resonance apparatus. PBS buffer was injected into the apparatus, followed by confirmation of a baseline. (The resonant angle obtained thereupon was designated as a reference point). Thereafter, a series of injections of the following solutions was repeated 3 times in the following order: injection of an aqueous solution containing 0.2 M EDC (1-(3-Dimethylaminopropyl)-3-ethylcarbodiimide) and 50 mM NHS (N-Hydroxysuccinimide), followed by stationary placement of the apparatus for 7 minutes; injection of a PBS buffer, followed by stationary placement of the apparatus for 1 minute; injection of a 0.1 mg/ml CA solution (acetic acid buffer: pH 5.0), followed by stationary placement of the apparatus for 15 minutes; injection of a PBS buffer, followed by stationary placement of the apparatus for 1 minute; injection of a 1 M ethanolamine solution (Biacore), followed by stationary placement of the apparatus for 7 minutes; injection of a PBS buffer, followed by stationary placement of the apparatus for 1 minute; and injection of 10 mM NaOH, followed by stationary placement of the apparatus for 1 minute. At the end, PBS buffer was injected the apparatus, followed by stationary placement of the apparatus for 1 minute. The difference between the resonant angle obtained thereupon and the resonant angle corresponding to the original point was determined to indicate the amount of CA immobilized. Herein, "1RU" represents a resonant angle of a degree of $\frac{1}{10000}$.

The amounts of CA immobilized were 5200 RU (sample 1) and 5000 RU (sample 2). Thus, it has been found that it is possible to immobilize a large amount of protein even on a surface produced with the use of an SAM compound having high water solubility.

Example 4

Example 4 relates to nonspecific adsorption of a low-molecular-weight compound to the sensor samples obtained in Example 2 and Comparative example 1. As the low-molecular-weight compound, CGP74514 (which is an inhibitor of Cyclin-Dependent Kinase) and Tween 20 (which is a surfactant) were selected. Then, capacity for suppression of nonspecific adsorption on the surface of each sensor sample was examined.

Samples 1 and 2 that had been produced in Example 2 and Comparative example 1, respectively, were introduced into a surface plasmon resonance apparatus. PBS buffer was injected thereinto, followed by confirmation of a baseline. (The resonant angle obtained thereupon was designated as a reference point). A PBS buffer solution of CGP74514 (50 μM) or a PBS buffer solution of Tween 20 (0.005% by weight) was injected into the apparatus, followed by stationary placement of the apparatus for 2 minutes. At the end, a PBS buffer was injected into the apparatus, followed by stationary placement of the apparatus for 2 minutes. The difference between the resonant angle obtained thereupon and the resonant angle corresponding to the original point was determined to indicate the amount of low-molecular-weight compound nonspecifically adsorbed.

As the amount of low-molecular-weight compound nonspecifically adsorbed by sample 1, 3RU of CGP74514 and 5RU of Tween 20 were obtained. As the amount of low-molecular-weight nonspecifically compound adsorbed by sample 2, 5RU of CGP74514 and 9RU of Tween 20 were obtained. It has been found that it is possible to suppress nonspecific adsorption of a low-molecular-weight compound even on a surface produced with the use of an SAM compound having high water solubility.

INDUSTRIAL APPLICABILITY

In accordance with the present invention, it is possible to reduce the amount of solvent used by using a water-soluble SAM compound. In addition, burdens on the global environment are reduced and production environments are improved. Further, since a small amount of solvent is used, even in a case in which a sensor substrate is made of plastic, there is no problem in terms of the promotion of plastic degradation. Thus, it is possible to suppress noise during surface plasmon resonance measurement. Furthermore, a water-soluble SAM compound having a short carbon chain can easily be obtained at low cost. A large amount of protein can be immobilized on the biosensor of the present invention and nonspecific adsorption is less likely to be caused thereon.

The invention claimed is:

1. A method for producing a biosensor comprising a substrate on which a hydrophilic polymer having a reactive group capable of binding to a physiologically active substance is immobilized via a compound represented by the following formula (1), said compound at a concentration of 1 mM being dissolved in water at 25° C.:

X-L-Y (1) 

wherein X represents a group capable of binding to metal, L represents a linking group, and Y represents a functional group to which the hydrophilic polymer is bound, which comprises a step of coating the substrate with a solution of the compound represented by formula (1) in water, and a step of allowing the hydrophilic polymer having a reactive group capable of binding to a physiologically active substance to come into contact with the substrate coated with the solution of the compound represented by formula (1), thereby allowing the hydrophilic polymer to bind to the compound represented by formula (1).

2. The method according to claim 1, wherein the substrate is coated with a mixture of alkanethiol having an amino group and alkanethiol having a hydrophilic group, and the hydrophilic polymer is allowed to bind to alkanethiol having an amino group.

3. The method according to claim 1, wherein the hydrophilic group of alkanethiol having a hydrophilic group is a hydroxyl group or an oligoethylene glycol group.

4. The method according to claim 1, wherein the molar ratio of alkanethiol having an amino group to alkanethiol having a hydrophilic group in a mixture thereof is a molar ratio between 1:1 and 1:1,000,000.

5. The method according to claim 1, wherein the hydrophilic polymer having a reactive group capable of binding to a physiologically active substance is allowed to react with the compound represented by the formula (1) in such a state that a thin film of said polymer is formed on the substrate.

6. The method according to claim 5, wherein thin film is formed on the substrate by a spin coating method or a spray coating method.

7. The method according to claim 1, wherein the hydrophilic polymer is a polysaccharide.

8. The method according to claim 1, wherein the hydrophilic polymer is a carboxyl group-containing polysaccharide.

9. The method according to claim 1, wherein the film thickness of the hydrophilic polymer is 1 nm to 300 nm.

10. The method according to claim 1, wherein the average molecular weight of the hydrophilic polymer is 10,000 to 200,000.

11. A method for producing a biosensor comprising a substrate on which a hydrophilic polymer having a reactive group capable of binding to a physiologically active substance is immobilized via a compound represented by the following formula (2):

X-L$^1$-Y (2) 

wherein X represents a group capable of binding to metal, L$^1$ represents a C$_2$-C$_{10}$ linear alkylene group optionally interrupted by a hetero atom, and Y represents a functional group to which the hydrophilic polymer is bound, which comprises a step of coating the substrate with a solution of the compound represented by formula (2) in water, and a step of allowing the hydrophilic polymer having a reactive group capable of binding to a physiologically active substance to come into contact with the substrate coated with the compound represented by formula (2), thereby allowing the hydrophilic polymer to bind to the compound represented by formula (2).

12. The method according to claim 11, wherein the hydrophilic polymer is a polysaccharide.

13. The method according to claim 11, wherein the hydrophilic polymer is a carboxyl group-containing polysaccharide.

14. The method according to claim 11, wherein the film thickness of the hydrophilic polymer is 1 nm to 300 nm.

15. The method according to claim 11, wherein the average molecular weight of the hydrophilic polymer is 10,000 to 200,000.

16. A method for immobilizing a physiologically active substance on a biosensor, which comprises a step of allowing the biosensor and the physiologically active substance to come into contact with each other, thereby allowing the physiologically active substance to bind to the biosensor, wherein the biosensor comprises a substrate on which a hydrophilic polymer having a reactive group capable of binding to a physiologically active substance is immobilized via a compound represented by the following formula (1), said compound at a concentration of 1 mM being dissolved in water at 25° C.:

X-L-Y (1) 

wherein X represents a group capable of binding to metal, L represents a linking group, and Y represents a functional group to which the hydrophilic polymer is bound.

17. A method for detecting or measuring a substance interacting with a physiologically active substance, which comprises a step of allowing a biosensor, the surface of which the physiologically active substance is bound to via a covalent bond, to come into contact with the test substance for detecting or measuring, wherein the biosensor comprises a substrate on which a hydrophilic polymer having a reactive group capable of binding to a physiologically active substance is immobilized via a compound represented by the following formula (1), said compound at a concentration of 1 mM being dissolved in water at 25° C.:

$$X\text{-}L\text{-}Y \tag{1}$$

wherein X represents a group capable of binding to metal, L represents a linking group, and Y represents a functional group to which the hydrophilic polymer is bound.

18. The method according to claim 17 wherein the substance interacting with a physiologically active substance is detected or measured by surface plasmon resonance analysis.

* * * * *